United States Patent
Waterford et al.

(12)
(10) Patent No.: US 6,440,390 B2
(45) Date of Patent: *Aug. 27, 2002

(54) FORMULATIONS CONTAINING A PHOSPHIDE FOR USE IN THE CONTROLLED GENERATION OF PHOSPHINE

(75) Inventors: Colin Joseph Waterford, McGregor; Robert Gordon Winks, Nambour, both of (AU)

(73) Assignee: Commonwealth Scientific and Industrial Research Organisation, Australian Capital Territory (AU)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/313,732
(22) Filed: May 18, 1999

Related U.S. Application Data (63) Continuation-in-part of application No. 08/971,247, filed on Nov. 17, 1997, now abandoned, which is a continuation of application No. 08/343,609, filed on Jan. 6, 1995, now abandoned, which is a continuation of application No. PCT/AU93/00270, filed on Jun. 4, 1993.

(30) Foreign Application Priority Data

| | | |
|---|---|---|
| Jun. 5, 1992 | (AU) | PL2830/92 |
| Nov. 16, 1992 | (AU) | PL5821/92 |
| Mar. 19, 1993 | (AU) | 51616/93 |
| Jun. 1, 1993 | (ZA) | 93/3931 |
| Jun. 4, 1993 | (BR) | 9306500 |
| Jun. 4, 1993 | (CA) | 2137074 |
| Jun. 4, 1993 | (EP) | 93912420 |
| Jun. 4, 1993 | (HU) | 9403462 |
| Jun. 4, 1993 | (JP) | 6-50095 |
| Jun. 4, 1993 | (JP) | 6-500957 |
| Jun. 4, 1993 | (RU) | 94046233 |
| Jun. 4, 1993 | (UA) | 94129118 |
| Jun. 4, 1993 | (WO) | PCT/AU93/00270 |
| Jun. 7, 1993 | (TH) | 019170 |
| Dec. 7, 1993 | (CN) | 93119910 A |

(51) Int. Cl.$^7$ .......... A01N 25/06; A01N 25/20; A01N 25/18; A01N 59/26; A61K 9/72
(52) U.S. Cl. .......... 424/40; 424/405; 424/601; 424/682
(58) Field of Search .......... 424/40, 405, 601, 424/682

(56) References Cited

U.S. PATENT DOCUMENTS 4,200,657 A  4/1980  Cook (List continued on next page.)

FOREIGN PATENT DOCUMENTS

DD  11650  6/1956

(List continued on next page.)

OTHER PUBLICATIONS

A. R. Green et al. "The Flammability Limit of Pure Phosphine–Air Mixtures at Atmospheric Pressure" published in Controlled Atmosphere and Fumigation in Grain Storages (edited by B.E. Ripp et al.), Amsterdam, Elsevier, 1983, pp. 433–449.

*Primary Examiner*—Carlos Azpuru
(74) *Attorney, Agent, or Firm*—Ladas & Parry (57) ABSTRACT

A formulation for use in the controlled generation of phosphine comprises a mixture of a particulate phosphide and a water-immiscible compound. The water-immiscible compound is paraffin oil, petroleum jelly, a mixture of these materials or a wax having a melting point in the range 35° C. to 65° C. The phosphide comprises from 65 to 85 per cent (by weight) of the formulation. Such a formulation can be added progressively to water in a reaction chamber. Alternatively, the formulation can be packaged in a water-impermeable container from which a region can be removed to expose the formulation to water vapor in a gas flowing past the container. The water or the water vapor reacts with the phosphide particles as they become exposed to form phosphine. The phosphine, mixed with a carrier (usually air), may be fed into a duct connected to a grain silo, for fumigation of grain stored in the silo.

31 Claims, 9 Drawing Sheets

U.S. PATENT DOCUMENTS

| | | |
|---|---|---|
| 4,756,117 A | 7/1988 | Friemel |
| 4,863,718 A | 9/1989 | Bernardo |
| 5,015,475 A | 5/1991 | Kapp et al. |

FOREIGN PATENT DOCUMENTS

| | | |
|---|---|---|
| DD | 271012 | 8/1989 |
| DE | 880 817 | 6/1953 |
| DE | 2952921 | 2/1980 |
| EP | 0318040 | 5/1989 |
| FR | 750 035 | 8/1933 |
| GB | 333 216 | 8/1930 |
| WO | 91/00017 | 1/1991 |
| WO | 91/19671 | 12/1991 |
| WO | 93/25075 | 12/1993 |
| WO | WO93/25075 | * 12/1993 |

* cited by examiner

FORMULATIONS CONTAINING A PHOSPHIDE FOR USE IN THE CONTROLLED GENERATION OF PHOSPHINE

CROSS-REFERENCE

This application is a continuation-in-part of U.S. patent application Ser. No. 08/971,247, now abandoned, filed Nov. 17, 1997, which was a continuation of U.S. patent application Ser. No. 08/343,609 now abandoned, filed Jan. 6, 1995, which was a continuation of International patent application No. PCT/AU93/00270, which was filed on Jun. 4, 1993.

TECHNICAL FIELD

This invention concerns formulations for use in the generation of phosphine. These formulations are particularly suited for the production of phosphine for use in the fumigation of grain and similar particulate commodities stored in bulk, but they are not limited to that purpose.

BACKGROUND TO THE INVENTION

Phosphine ($PH_3$) has been a preferred gaseous fumigant for stored grain and similar particulate commodities because any residue of the fumigant will be lost or oxidised to a harmless phosphate when the grain or other commodity is processed to produce a food. Examples of the fumigation of grain with phosphine are found in the specifications of: International patent application No. PCT/AU90/00268 (which is WIPO Publication No. WO 91/00017); U.S. Pat. Nos. 4,059,048, 4,200,657, 4,756,117 and 4,812,291; and Australian patent No.598,646 and its equivalent South African patent No. 86/4806. This list is not exhaustive.

The phosphine used to fumigate a grain silo or other storage may be supplied by cylinders which contain phosphine or (more usually) a mixture of phosphine and carbon dioxide. Alternatively, the phosphine may be supplied by on-site generators in which phosphine is produced by the reaction of water or water vapour with a metal phosphide (typically aluminium phosphide or magnesium phosphide). However, the more traditional technique for disinfecting a grain silo or the like with phosphine involves the use of a probe to position formulations of aluminium phosphide or magnesium phosphide within the grain mass, where moisture in the air circulating through the grain reacts with the phosphide in the formulation to generate phosphine.

A modification of this technique involves the placement of pellets of a metallic phosphide in the head space of a grain silo. The phosphine produced when the phosphide reacts with moisture in the atmosphere above the grain is circulated through the stored grain either by the natural convection currents that are present in the silo or by active recirculation of air from the head space through the grain using recirculation ducts. Examples of this approach are found in the aforementioned specifications of U.S. Pat. Nos. 4,200,657 (to J S Cook) and 4,756,117 (to W. Friemel). Such techniques, however, cannot be guaranteed to supply phosphine to all regions of the bulk stored grain to eradiate weevils and other unwanted grain pests. In addition, when these traditional techniques are used, there is no control over the concentration of phosphine in the grain after the phosphide formulation has been added, and there is no possibility of regulating the phosphine concentration/time regime in the bulk storage to be most effective.

When using phosphine from cylinders which contain this gas (they usually contain 2 per cent phosphine and 98 per cent carbon dioxide), the phosphine should be mixed with air externally of the stored grain and the resultant gas mixture should then be pumped through the grain. This method of disinfestation of the grain should be carried out periodically, or whenever it is perceived that fumigation of the grain is necessary or desirable. Although this approach to the fumigation of grain is regarded as the most efficient, its major disadvantage is the need to guarantee a supply of expensive cylinders of the gas mixture to the treatment site.

There is one significant problem with the use of phosphine. When its concentration in air reaches certain values, the gas mixture is flammable and potentially explosive. The generally accepted maximum safe concentration of phosphine in air at standard temperature and pressure is 1.79 per cent by volume. The paper entitled "The Flammability Limit of Pure Phosphine-Air Mixtures at Atmospheric Pressure", by A. R. Green et. al., which was published in "Controlled atmosphere and fumigation in grain storages" (Edited by B. E. Ripp et. al.), Elsevier, 1983, pages 433–449, confirms this safe concentration limit and provides further information about the flammability of phosphine.

Other potential problems with the use of phosphine are the toxicity of phosphine to mammals when the phosphine is present in high concentrations, and the exothermic nature of the hydrolysis reaction which produces the phosphine.

Thus the use of on-site phosphine generators, such as the generator described in European Patent Publication No. A-0318040 (the specification of European patent application No. 88119701.6), presents a number of hazards to the user. In addition, with the fumigation regimes now being employed (for example, maintaining low phosphine concentrations for long periods), it is possible that the on-site phosphine generators may be left unattended for a considerable time. This is particularly likely to be the situation when the phosphine generator is used for the fumigation of storages at remote locations. Thus on-site phosphine generators, with their attendant fire or explosion risk, have been unattractive for long term fumigation operations.

It is an objective of the present invention to provide formulations of a reactive phosphide which are inherently safe for storage and/or transportation and which can be added periodically to water, or over which moist air can be passed, so that phosphine is generated in a controlled manner. In achieving this objective, the present invention provides an alternative to the phosphine generation systems (which use either phosphides in powder form positioned within a chamber closed by a membrane which is porous to moisture and phosphine, or the periodic dropping of pellets of phosphide into a water bath) which are described in the specifications of International patent application No. PCT/AU91/00264 (which is WIPO publication No. WO 91/19671) and its equivalent U.S. Pat. No. 5,573,740.

The present invention achieves this objective by mixing together a particulate phosphide and a water-immiscible compound which is inert with respect to the phosphide. The water-immiscible compound may be petroleum jelly or a non-volatile oil (for example, paraffin oil), or a mixture of petroleum jelly and a non-volatile oil. Preferably, however, the water-immiscible compound is a wax which has a melting point in the range of from about 35° C. to about 65° C.

If the water-immiscible compound is petroleum jelly and/or a non volatile oil, the quantity of water-immiscible compound in the formulation must be sufficient to ensure that the formulation is capable of being extruded through an orifice (for example, for feeding into a water bath) at the temperature of use of the formulation.

In some uses of the formulation, moisture-laden warm air will be passed over a sample of such a formulation. Thus a sample of the formulation must slump in a controlled manner (to expose the phosphide particles in the formulation) at its temperature of use. These constraints mean that the particulate phosphide must comprise from about 65 per cent (by weight) to about 85 per cent (by weight) of the formulation, and is preferably in the range of from 70 to 75 per cent (by weight) of the formulation. These phosphide concentrations have also been found to be appropriate when the water-immiscible compound of the formulation is a wax having a melting point in the specified range.

When a formulation in accordance with this invention, having petroleum jelly and/or a non-volatile oil as its water-immiscible compound, is placed in a water bath, or in a moist air flow, the covering of the phosphide particles (which may be pellets) is at least partially dispersed. Water, in liquid or vapour form, then comes into contact with the exposed phosphide, and reacts with it to form phosphine and a hydroxide.

If, however, a sample of the formulation which has a wax as its water-immiscible compound is placed in a water bath or in a flow of moist gas (moist air), (a) if the formulation sample has exposed phosphide particles at its surface, the water (in liquid or vapour form) comes into contact with the exposed phosphide and reacts with it to form phosphine and a hydroxide; but (b) if there is no exposed phosphide particle at the surface of the formulation sample (for example, because the sample was given a thin coating of the wax used in the formulation), the water, in liquid or vapour form, must first expose the phosphide particles near the surface of the formulation by melting the wax (or the surface of the formulation has to be scratched or a shaving has to be removed from it) to allow the water to contact and react with the exposed phosphide and form phosphine and a hydroxide.

Thus, according to the present invention, there is provided a phosphide formulation for use in the controlled production of phosphine, the formulation comprising a mixture of:

(a) a particulate phosphide which reacts with water to form phosphine; and (b) a water-immiscible compound which is inert with respect to the phosphide, said water-immiscible compound being selected from the group consisting of (i) petroleum jelly; (ii) a non-volatile oil; (iii) a mixture of a non-volatile oil and petroleum jelly; and (iv) a wax having a melting point in the range of from about 35° C. to about 65° C.;

the particulate phosphide in the formulation comprising from about 65 per cent (by weight) to about 85 per cent (by weight) of the formulation.

Any suitable phosphide may be used in this formulation. The specifications of aforementioned Australian patent No. 598,646 and South African patent No. 86/4806 state that phosphine for fumigation of grain silos and similar bulk storage structures can be generated by "the hydrolysis of phosphides, such as those of calcium, magnesium, aluminium, zinc and tin . . . ". In practice, a phosphide that is suitable for inclusion in the formulation will be selected from materials that are available at a reasonable cost.

Thus, the person who "performs the invention" (that is, the person who makes up the formulation for the controlled generation of phosphine) will select a phosphide from the materials that are available, bearing in mind the manner in which the invention will be used. For example, when the formulation is to be used in Australia for the fumigation of grain (this is the main area of interest to the present inventors), aluminium phosphide or magnesium phosphide will be used in the formulations because these phosphides (i) are readily available in Australia, (ii) are relatively low priced phosphides, and (iii) do not leave unacceptable residues. If the phosphine is to be produced slowly, aluminium phosphide would be preferred since magnesium phosphide reacts with water more rapidly than aluminium phosphide. However, in China, calcium phosphide may be preferred, for it is understood by the present inventor that calcium phosphide is more commonly available in that country. Zinc phosphide may be used only if the phosphine is produced at a slow rate, or in conditions that ensure that a significant concentration of diphosphine (which is also produced when zinc phosphide reacts with water, and which is spontaneously flammable) is not generated.

In view of the country of origin of this invention, the examples in the description of the invention refer only to aluminium phosphide or magnesium phosphide in the formulations.

The size of the particles of the phosphide in the formulation is not critical. In the initial experimentation with formulations in which the water-immiscible compound was petroleum jelly and/or a non volatile oil, to prove the efficacy of this invention, the present inventors limited the phosphide particles to a maximum diameter of 250 $\mu$m by sieving, because they found this to be a useful size limitation when producing a formulation having an extrudable paste consistency. However, they quickly found that technical grade aluminium and magnesium phosphides, which have a significant proportion of particles with a diameter in excess of 250 $\mu$m, can be used successfully in the formulations. Indeed, it has been found that, for the rapid (but controlled) production of phosphine over a significant period of time, small pellets of a phosphide can be used in the formulation.

If the water-immiscible compound of the formulation is a wax which has a melting point in the range of from about 35° C. to about 65° C. (such a wax, in this specification, will be termed a "low melting point wax"), the formulation will be a solid at ambient temperatures. When a thin coating of the same wax is applied to a block of this formulation, it is particularly suitable for transportation because the phosphide in the formulation is unaffected by moisture which may come into contact with the wax coating in the normal course of handling. Another benefit of this formulation, in which phosphide particles are located within a matrix of low melting point wax, is that it can readily be made into pellets. Such pellets can be used in the same manner as pellets of other phosphide formulations have been used previously (see, for example, the aforementioned specifications of International patent application No. PCT/AU91/00264 and U.S. Pat. No. 5,573,740). This is because, as noted previously, if the surfaces of the pellets contain exposed aluminium phosphide particles, water vapour (or water if the pellets are dropped into a water bath) can react with the exposed particles to generate phosphine and leave an insoluble hydroxide. When this occurs , there is a small volume increase of the reacted particles. This volume increase at the surface of a pellet distorts the surface and effectively provides the water vapour (or liquid) with access to the phosphide particle or particles directly "underneath" the surface particle. This effect occurs progressively through the pellet, thus ensuring a controlled release of phosphine from each pellet.

A particular advantage of this expansion as a particle is converted from the phosphide to the hydroxide is that it makes it possible to select a surface area of the pellets—or of a block of the formulation—according to the required rate of phosphine production. The greater the surface area, the higher the rate of phosphine production. A secondary benefit is that it is not necessary to heat the formulation to melt the wax to expose phosphide particles in the formulation. However, it should be noted that there are circumstances when it will be necessary to have the temperature of use of the formulation high enough to melt the wax. One such circumstance is when, because the formulation has to be stored for some time before the pellets (or shavings from a block of the formulation, or one or more blocks of the formulation) are dropped into a hot water bath to generate phosphine, a thin coating of wax has been applied to the formulation to protect it from possible deterioration due to the action of ambient air moisture during the storage period.

Thus it may be necessary to heat a formulation in accordance with the present invention which has a low melting point wax as its water-immiscible compound to soften its surface wax prior to its dispersion into a water bath, and/or it may be necessary to heat the water bath to a temperature which is high enough to maintain a softened state of the formulation and prevent is re-solidification, to ensure that the wax separates from the solid phosphide particles near the surface of the formulation, so that they come into contact with the water.

Any suitable low melting point wax may be used as the water-immiscible compound of the present invention. The selection of an appropriate wax will depend upon the availability and cost of the waxes from which a choice may be made.

The present inventors have found paraffin wax to be a convenient low melting point wax. Paraffin wax is a by-product of oil refining. It has a crystalline wax structure with oil held in suspension in the wax. The more oil in suspension, the lower the melting point of the wax. The present inventors have used paraffin waxes with melting points of 60° C., 55° C. and lower. Alternative waxes include candle waxes and thermostat waxes (such as those marketed in the U.S.A. by Astor Corporation) which have melting points within the range required for the present invention, polyester wax (which has a melting point of 37° C. and which was invented by Dr. A. F. Steedman of the University of Glascow), certain halocarbon waxes (such as the "600" wax marketed by Halocarbon Products Corporation of New Jersey, U.S.A.), and a range of embedding waxes used in histology and microscopy (for example, the "Tissue-Tek", "Paramat" and "Paraplast" waxes). Note: "Tissue-Tek", "Paramat" and "Paraplast" are trade marks. This list of waxes that may be used in the present invention is not exhaustive.

If the formulation of the present invention is to be introduced into a water bath to produce phosphine, an optional additive to the formulation is a surfactant, frothicant, wetting agent, or other compound which assists in the dispersal of the water-immiscible compound in the water bath, but which is inert with respect to the phosphide component of the formulation. Dispersal of the formulation in the water of a water bath may also be assisted by the addition of a detergent to that water.

It will be apparent from the foregoing that the formulations of the present invention may be used in phosphine generators in which a formulations as described above is controllably discharged from a container into a water bath, using a pump, screw feed (auger feed) or other suitable means.

Thus, the present invention encompasses a method of generating phosphine in a controlled manner which comprises causing a small quantity of a phosphide formulation in accordance with the present invention to be introduced periodically into a water bath containing water at a temperature such that the water-immiscible compound is removed progressively from the formulation so that the phosphide particles thereof are contacted by the water of the water bath, and react with the water of the water bath to produce phosphine.

It will be necessary, sometimes, to store a formulation made in accordance with the present invention, or to transport a formulation to a grain silo or other storage structure in which the formulation is to be used. For these purposes, the phosphide formulation of the present invention may be contained in a sealed package (to ensure safe transportation and storage of the formulation). When the formulation is to be used to generate phosphine, the sealed package is opened or partially opened to expose the formulation to moist air or to another carrier gas which contains moisture (if necessary, at a temperature which causes the water-immiscible compound of the formulation to flow). The water in the air or carrier gas then reacts with exposed phosphide particles in the formulation to produce phosphine. Using this technique, the phosphine is produced in a predicable manner, the rate of phosphine production being controlled by regulating the exposed surface of the formulation, the composition of the formulation, and the water content and temperature of the air or other carrier gas.

Such a "packaged" formulation can be included in existing ducting to a grain silo or other fumigation enclosure. Alternatively, it can be dropped into a water bath, to produce phosphine which is fed into ducting connected to a grain silo or other enclosure.

Another way of using the packaged formulation is to place it within a fumigation enclosure, so that moisture in the air within the enclosure can react with the phosphide in the formulation to generate phosphine.

Thus the present invention also encompasses a formulation as defined above, packaged within a moisture-impervious container, said container having at least one aperture therein, the (or each) aperture being closed by a moisture-impervious closure member, the (or each) closure member being removable to expose the formulation packed in the container.

Still further according to the present invention, there is provided a method of generating phosphine which comprises the steps of (a) placing a packaged phosphide formulation, as recited in the last preceding paragraph, within a duct, chamber or the like through which a gas can flow, the removable region (or one of the removable regions) of the container being subsequently or previously removed from the container in which the formulation is packed; and (b) causing a moisture-containing carrier gas to flow through said duct, chamber or the like and past the exposed phosphide formulation, whereby the water in the carrier gas reacts with the phosphide in the formulation to form phosphine, which is incorporated into the carrier gas.

Examples of formulations in accordance with the present invention and their properties, and embodiments of the methods of the present invention, will now be described, by way of example, with reference to the accompanying drawings.

DETAILED DESCRIPTION OF EXAMPLES OF THE INVENTION

To evaluate phosphide formulations prepared in accordance with the present invention, quantities of technical grade aluminium phosphide were mixed with various water-immiscible compounds, or mixtures of water-immiscible compounds, and the resultant formulations were dispersed in water or were exposed to moist air in a variety of experimental conditions. Initially, the aluminium phosphide was ground and only aluminium phosphide particles which passed through a sieve having a mesh size of 250 $\mu$m were used in the formulations. However, later samples of the formulations were produced using aluminium phosphide which contained particles having a diameter greater than 250 $\mu$m. In addition, a small number of formulations were prepared by dispersing pellets of aluminium phosphide (marketed under the trade mark PHOSTOXIN) in selected water-immiscible compounds. All formulations tested yielded phosphine in a controlled manner when the formulations were placed in a water bath. In this regard, the size of the aluminium phosphide particles was found to be unimportant. However, the formulations prepared by mixing aluminium phosphide particles having a diameter of less than 250 $\mu$m with petroleum jelly and/or a non-volatile oil as the water-immiscible compound, were easiest to extrude through a nozzle.

All of the formulations that were obtained when the water-immiscible compound was paraffin oil, petroleum jelly, or a mixture of paraffin oil and petroleum jelly, had a paste-like consistency at ambient temperatures and at temperatures a little above ambient. Formulations having an aluminium phosphide content of from 65 per cent by weight to 85 per cent by weight were found to be convenient to handle and have a useful capacity to produce phosphine. The preferred content of aluminium phosphine was found to be from 70 per cent to 75 per cent if the formulation was to be extruded. If the formulation was to be packaged, as described later in this specification, then the preferred phosphide content was from 70 per cent to 80 per cent (Note: when specifying the composition of formulations, all percentages quotes in this specification are by weight).

A small quantity of CAB-O-SIL (trade mark) fumed silica was added as a thickening agent to some phosphide formulations prepared using paraffin oil as the water-immiscible compound. Earlier experimental work had shown that paraffin oil containing from 0.5 to 6.5 wt per cent fumed silica had a viscosity such that the mixture ranged from being almost indistinguishable from paraffin oil (with 0.5 per cent fumed silica) to a stiff gel (at 6.5 per cent fumed silica). It was found that when fumed silica was included in the paraffin oil used to prepare formulations of the present invention, only paraffin oil containing from 0.5 to 1.0 per cent fumed silica produced formulations which were extrudable. Furthermore, when small samples of these extrudable formulations were wetted with water, the samples broke up and reacted vigorously with a noticeable rise in temperature. When samples of the non-extrudable formulations containing fumed silica were added to a water bath stirred with a magnetic stirrer, the formulations (a) reacted vigorously after five minutes, and (b) produced a phosphine polymer at the surface of the water bath. Thus use of fumed silica as a thickening agent for formulations of the present invention is not recommended.

The effect of adding a surfactant to the water-immiscible material has also been investigated. As expected, the inclusion of a surfactant increased the reaction rate when the formulation was added to a water bath. In one example, the addition of polyethylene glycol to petroleum jelly, to produce a water-immiscible material comprising about 75 per cent petroleum jelly and 25 per cent polyethylene glycol, produced a formulation which, when immersed in water, had a significantly increased reaction rate when compared with similar formulations prepared with paraffin oil and petroleum jelly. The inclusion of a surfactant in quantities of up to 10 per cent of the total weight of the formulation, therefore, is believed to be advantageous when the formulation is required to generate phosphine quickly, particularly when the formulation is to be packaged and subsequently exposed to moist air.

In general, the wax content of formulations in accordance with the present invention which have a low melting point wax as the water-immiscible compound, determines the rate of production of phosphine. The lower the wax content, the higher the phosphide reaction rate and thus the higher the rate at which phosphine is produced.

In one experiment, conducted to demonstrate that the phosphine production rate can also be controlled by the surface area of a formulation in which phosphide particles are held within a matrix of a low melting point wax, a bulk formulation comprising 73 per cent (by weight) aluminium phosphide and 27 per cent (by weight) paraffin wax was prepared. One portion of this formulation was pressure moulded into discs, each having a radius of 4.4 cm, a thickness of 1.8 cm, and a mass of 150 grams. Another portion of this formulation was pressure moulded into cylinders, each having a radius of 2.7 cm, a height of 4.5 cm, and a mass of 140 grams.

When one of the discs was immersed in a reaction vessel containing water heated to 28° C., to which had been added 5 per cent of a detergent marketed under the trade mark "TEEPOL", phosphine was produced at an average rate of 1 gram per hour for 38 hours. When a cylinder of the formulation was added to the water in the reaction vessel, which was also at a temperature of 28° C. and which also contained 5 per cent of the detergent "TEEPOL", phosphine was produced at a rate which varied between 0.20 gram per hour and 0.40 gram per hour for a period of seven days.

Figure 1:
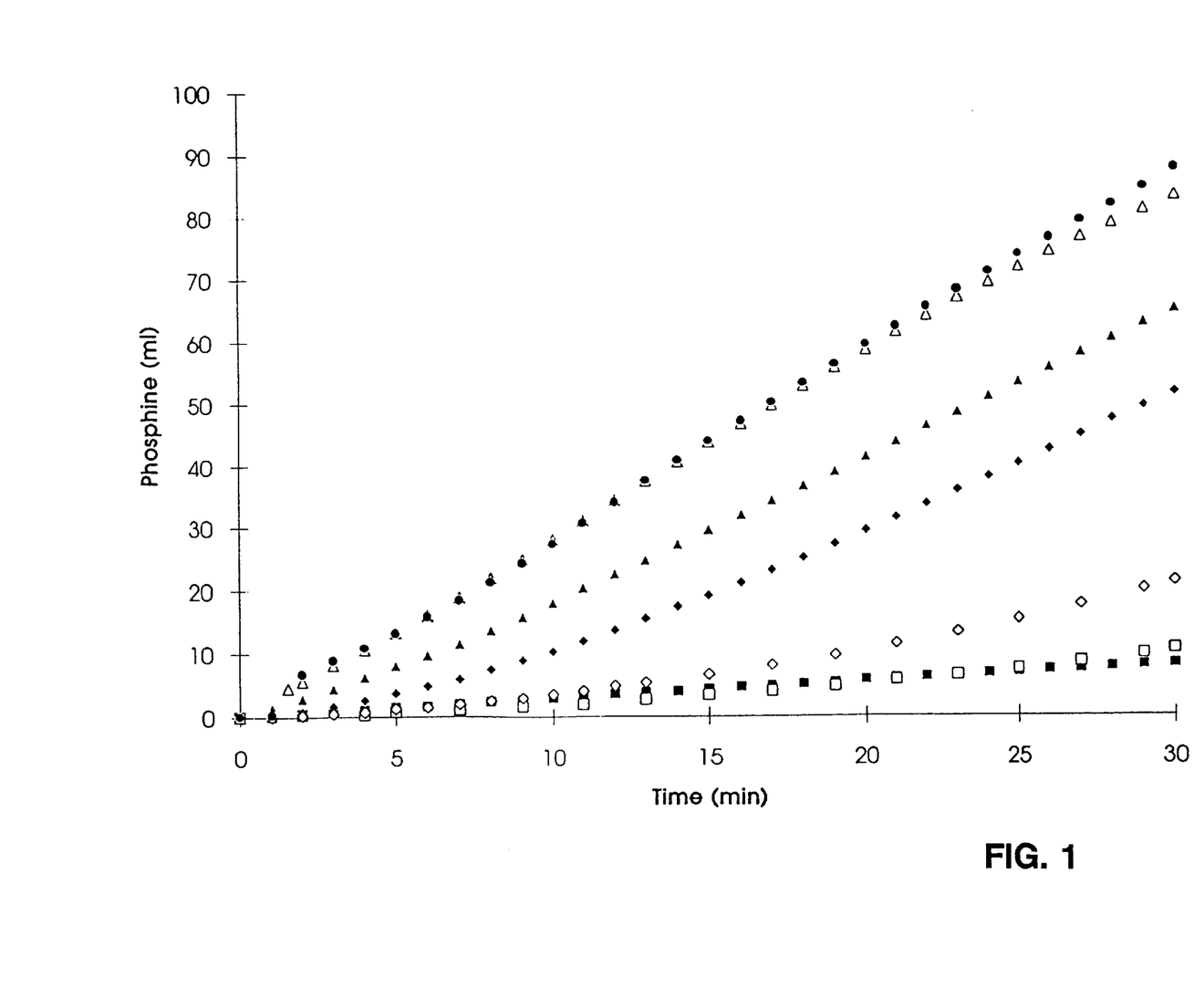
FIG. 1 is a graph showing the cumulative volume of phosphine produced in a period of 30 minutes by samples of phosphide formulations which have been placed in water which is not stirred.
Figure 2:
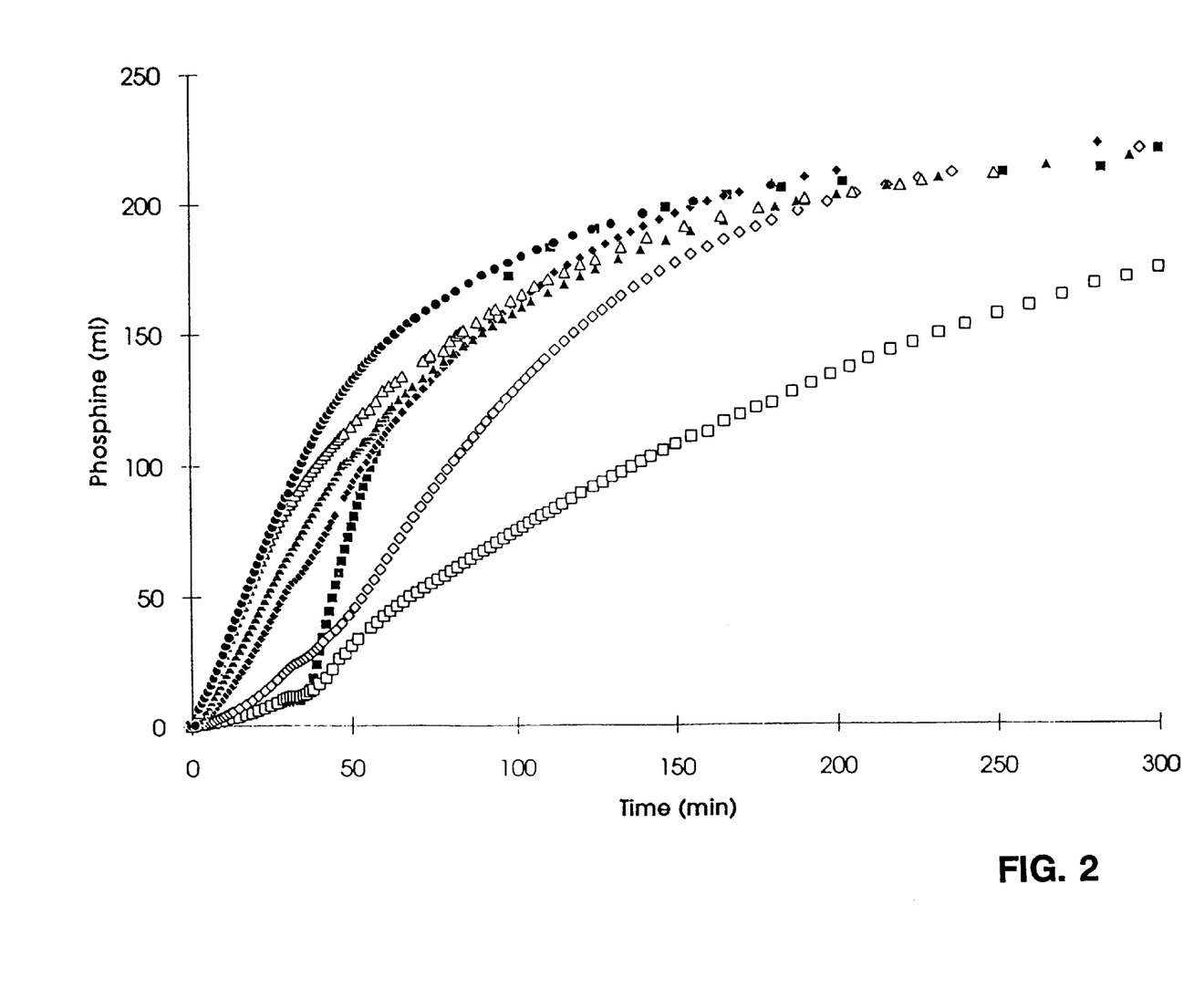
FIG. 2 is an extension of the graph of FIG. 1, showing the change in phosphine production when the water is stirred, 30 minutes after immersion of the phosphide formulations.

In one series of experiments, samples of the formulations prepared using petroleum jelly and/or paraffin oil as the water-immiscible compound, each weighting 1 gram and containing 0.73 gram of phosphide, were placed in a water bath at 23° C. and the cumulative volume of the phosphine released was measured over a period of 300 minutes. In one experiment in this series (a comparison experiment), a sample consisting of 0.73 gram aluminium phosphide, with no water-immiscible compound added, was placed in the water bath. In each experiment in this series, the water of the water bath was stirred continuously for the first 30 minutes. In some experiments, a detergent, either COMPROX (trade mark) or TEEPOL (trade mark), was added to the water in the bath before the experiment was conducted. A selection of the results obtained in this series of experiments is shown in FIGS. 1 and 2. FIG. 1 presents the data obtained in the first 30 minutes only of the experiments. FIG. 2 provides the data for the entire five hours of the experiments. The formulations from which these data were obtained, and the additives in some of the water baths used, are detailed below in Table 1.

TABLE 1

Key for the Data Presented in FIGS. 1 and 2

| Data shown by | Formulation aluminium phosphide | water-immiscible material | Additive in water bath |
|---|---|---|---|
| open squares | 73% | 27% paraffin oil | 3% COMPROX* |
| solid squares | 73% | 27% paraffin oil | nil |
| open diamonds | 73% | 27% petroleum jelly | nil |
| solid diamonds | 73% | 27% paraffin oil | 6% TEEPOL* |
| open triangles | 73% | 20.25% petroleum jelly 6.75% polyethylene glycol | nil |
| solid triangles | 73% | 27% petroleum jelly | 6% TEEPOL* |
| solid circles | 100% | nil | nil |

*Trade Mark

As shown by the data in FIG. 1, the aluminium phosphide powder with no water-immiscible compound produced its phosphine relatively quickly. The formulation comprising aluminium phosphide and paraffin oil produced phosphine at the slowest rate for the first 30 minutes, but once the water in the water bath was stirred, this formulation increased its rate of production of phosphine rapidly when there was no additive in the water bath, so that one hour after the start of the experiment with this formulation, the total volume of phosphine produced was comparable to that produced by most of the other formulations (the exceptions being the formulation containing 27 per cent petroleum jelly, when in a water bath with no additive, and the formulation containing 27 per cent paraffin oil in a water bath containing 3 per cent COMPROX).

The reason for the slower production of phosphine from formulations immersed in water containing the detergent COMPROX is not fully understood. The inclusion of heptane (a solvent) in the water had a similar effect on the rate of production of phosphine. It is believed that the COMPROX detergent, and also the heptane, reacts with the water-immiscible compound to form another protective layer around the phosphide particles. Only when the water has removed that additional protective layer can the water react with the phosphide to produce phosphine. Thus selection of an additive for the water can be used to increase, or decrease, the rate of production of phosphine using a formulation of the present invention.

The formulation which included polyethylene glycol in addition to its water-immiscible material had a phosphine production rate which was closest to that of aluminium phosphide powder.

Figure 3:
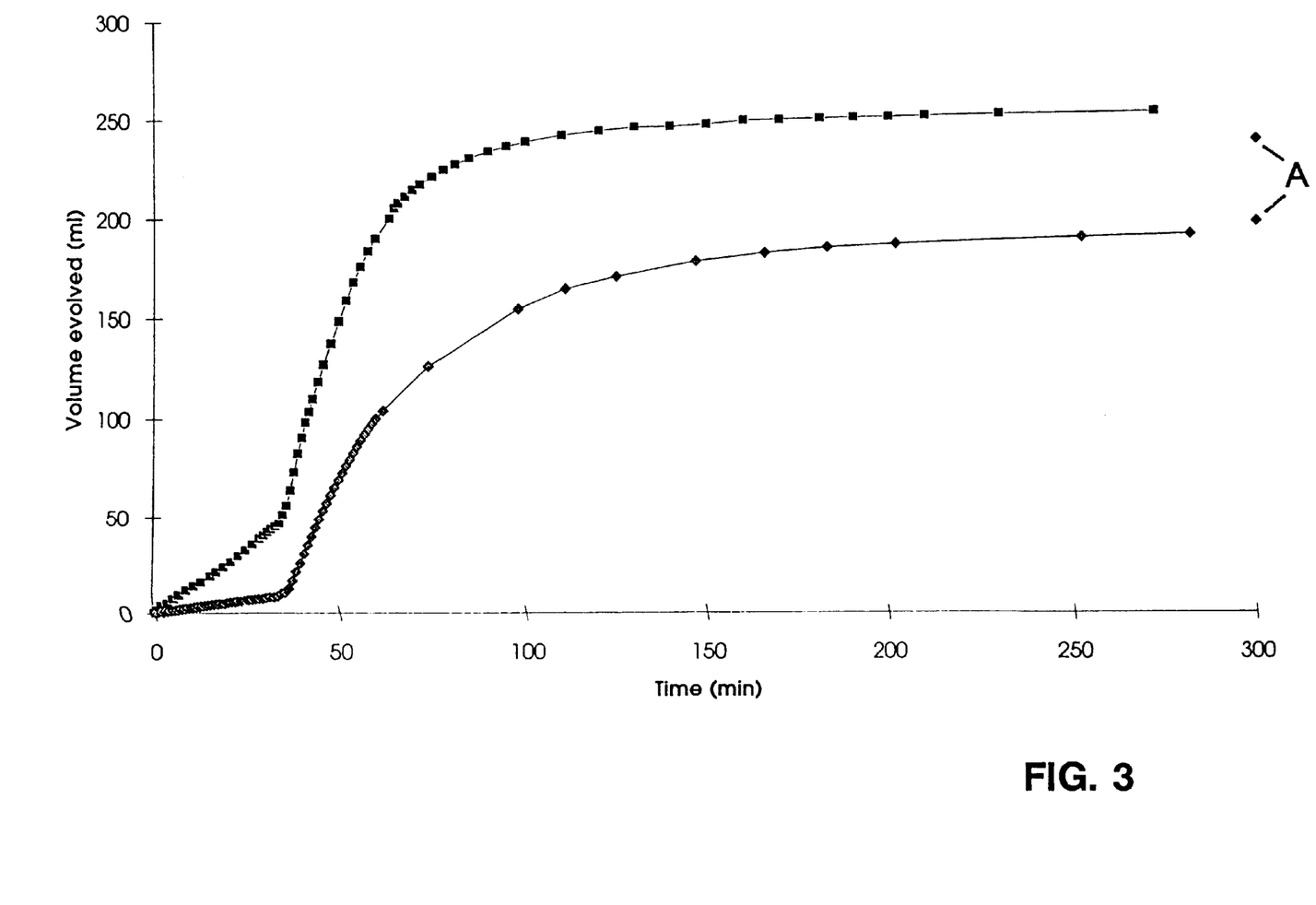
FIG. 3 shows the variation of phosphine production when identical samples of a phosphide formulation are immersed in water at different temperatures.

Some of the experiments of this series were repeated with the water bath at 40° C. FIG. 3 shows the data obtained at both 23° C. and 40° C. when the formulation used was 73 per cent aluminium phosphide and 27 per cent paraffin oil. The more rapid release of phosphine at the higher water bath temperature reflects the fact that at the higher temperatures, water removes the paraffin oil from the aluminium phosphide powder more quickly. The two data points shown by the reference A in FIG. 3 refer to measurements made a times later than 300 minutes with the water bath at 23° C., and show the gradual convergence of the two curves of FIG. 3.

Figure 4:
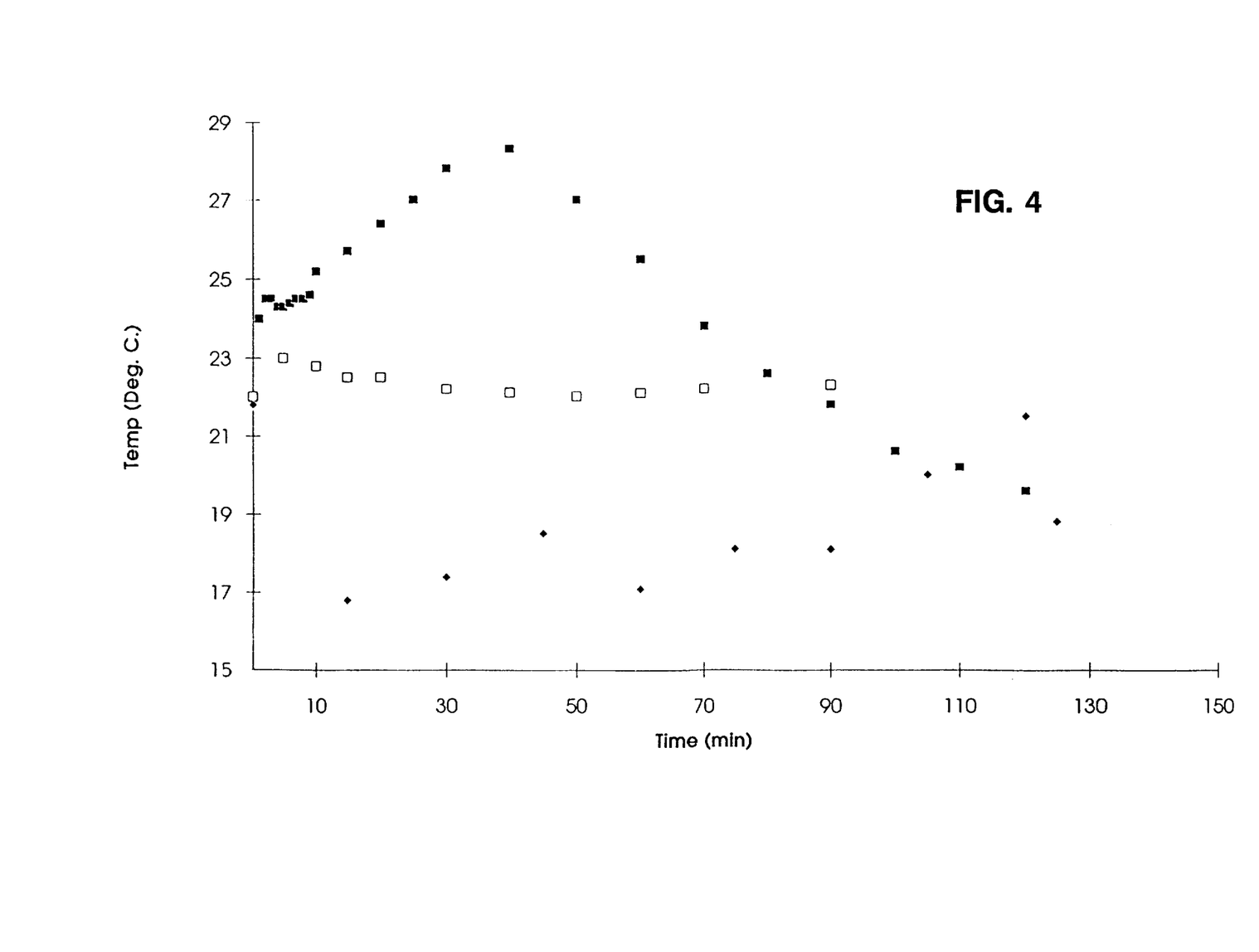
FIG. 4 presents data which illustrates the inherent safety of the formulations of the present invention.

To illustrate that formulations of the present invention are inherently safer to use than the pellets of aluminium phosphide that have traditionally been used to produce phosphine, samples of 25 grams each of (i) PHOSTOXIN pellets and (ii) a formulation of the present invention having the consistency of a thin paste, were immersed in respective, but essentially identical, water baths at a temperature of 22° C. In addition, water at a temperature of 22° C. was sprayed onto a 25 grams sample of the paste formulation. The observed variations in the temperature of the water with time are shown in FIG. 4, in which the solid squares show the data obtained with the PHOSTOXIN pellets, and the open squares present the measurements obtained when the formulation was immersed in water. It will be noted that the rapid production of phosphine by the pellets is accompanied by a significant increase in temperature, to the level where ignition of the phosphine is a possibility. In contrast to this, the production of phosphine by the formulation comprising aluminium phosphide and paraffin oil produced a small increase in temperature, and the spraying of the formulation with water actually reduced the water temperature.

To compare the rate at which phosphine is produced from PHOSTOXIN pellets and from pellets of a wax-based formulation in accordance with the present invention, sample pellets of PHOSTOXIN and pellets of the formulation of the present invention (having a low melting point wax as the water-immiscible compound and with the same phosphide content as the PHOSTOXIN pellets) were positioned in glass tubes through which moist air, having a relative humidity of 50 per cent, was passed. With the moist air flow rates used in this series of experiments, the PHOSTOXIN pellets had fully reacted in a period of from 1 day to 2 days. The pellets of the present invention produced phosphine at a much lower rate, but for periods of from 2 weeks to 2 months, depending on the wax content of the pellets and the moist air flow rate.

Two forms of apparatus for generating phosphine using an extrudable formulation in accordance with the present invention have been illustrated in, respectively, FIGS. 5 and 7 of the specification of International patent application No. PCT/AU93/00270 (WIPO publication No. WO93/25075). The information provided in that specification concerning that illustrated apparatus, and the operation thereof, is incorporated into the present specification by this reference thereto.

The packaged formulation aspect of the present invention is primarily (but not exclusively) for use in the storage and/or transportation of a formulation and in the generation of phosphine using a gas containing moisture. In the latter, control of the temperature and the relative humidity (moisture content) of the gas, and also of the area of the formulation that is exposed to the gas, enables the rate at which phosphine is produced to be controlled.

Figure 5:
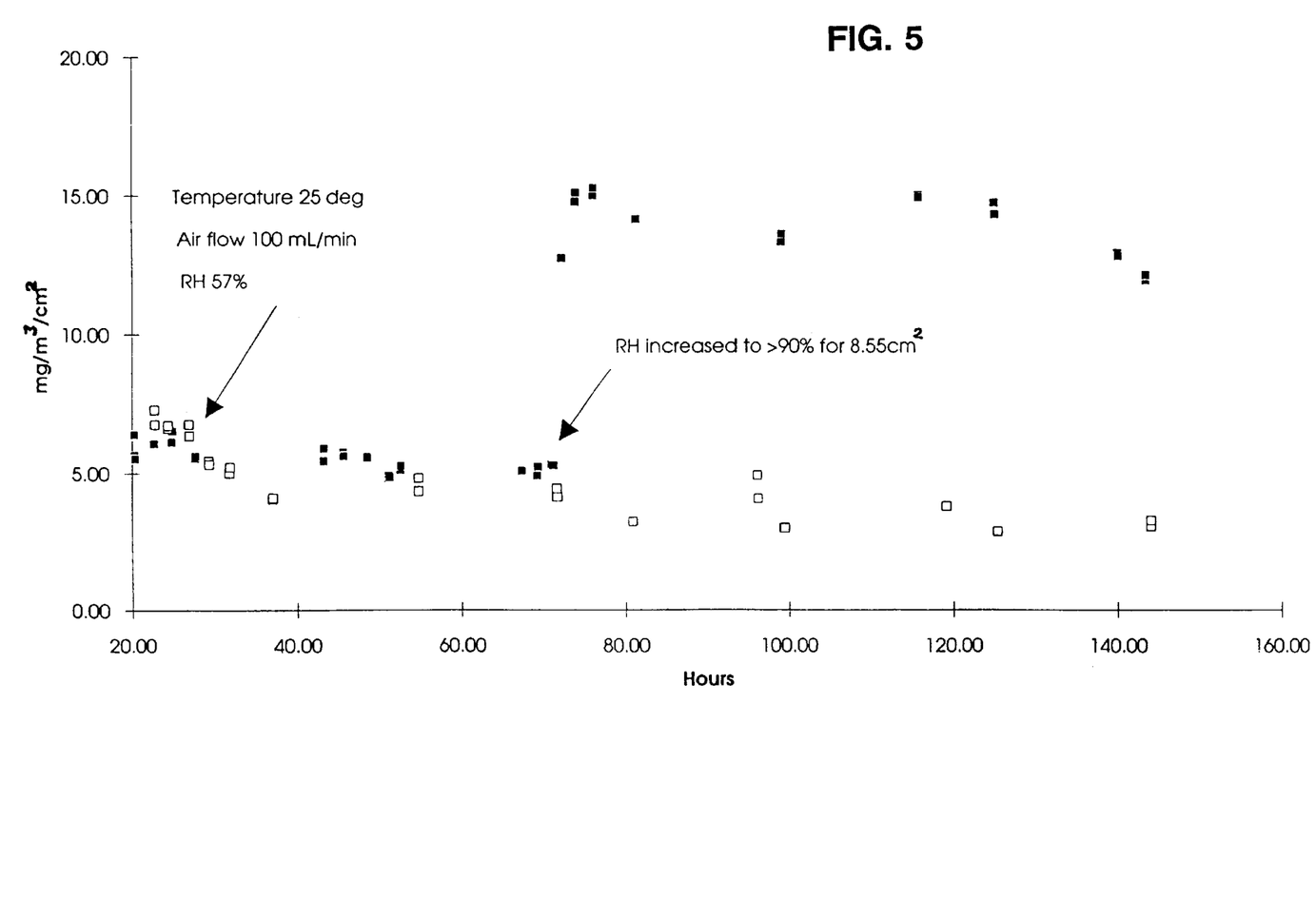
FIG. 5 illustrates how the phosphine output from a tray containing a sample formulation in accordance with the present invention varies when the relative humidity of the air flowing past the tray is changed.

A number of experiments have been undertaken by the present inventors in an investigation of the performance of packaged phosphide formulations. In one experiment, the rate of production of phosphine from formulations consisting of a paste comprising 73 per cent aluminium phosphide and 27 per cent paraffin oil, and having an exposed area of (i) 4.50 cm$^2$ and (ii) 8.55 cm$^2$, was investigated. The results obtained are presented in FIG. 5, in which the solid squares are data obtained with 8.55 cm$^2$ of the formulation exposed and the open squares present data obtained with 4.50 cm$^2$ of the formulation exposed. It should be noted that (a) the phosphine production shown in FIG. 5 is expressed in milligrams per cubic meter of gas flowing past the formulation, per square centimeter of exposed formulation (mg·m$^{-3}$·cm$^{-2}$);

(b) only the data obtained after steady state conditions had been established (20 hours after the formulations were first exposed to moist air) are presented in FIG. 5;

(c) the formulation with 4.5 cm$^2$ exposed was maintained at all times in an airflow of 100 ml·min$^{-1}$, having a temperature of 25° C. and a relative humidity of 57 per cent; and (d) the formulation with 8.5 cm$^2$ exposed was maintained at all times in an airflow of 100 ml·min$^{-1}$, having a temperature of 25° C., but the relative humidity of the air was changed from the initial value of 57 per cent to a value of greater than 90 per cent after 75 hours had elapsed since the start of the experiment.

It will be seen from FIG. 5 that the rate of production of phosphine per unit area of exposed formulation is the same for each sample of the formulation when the air flow and moisture content are the same. However, increasing the moisture content of the air results in a corresponding increase in the production of phosphine.

Figure 6:
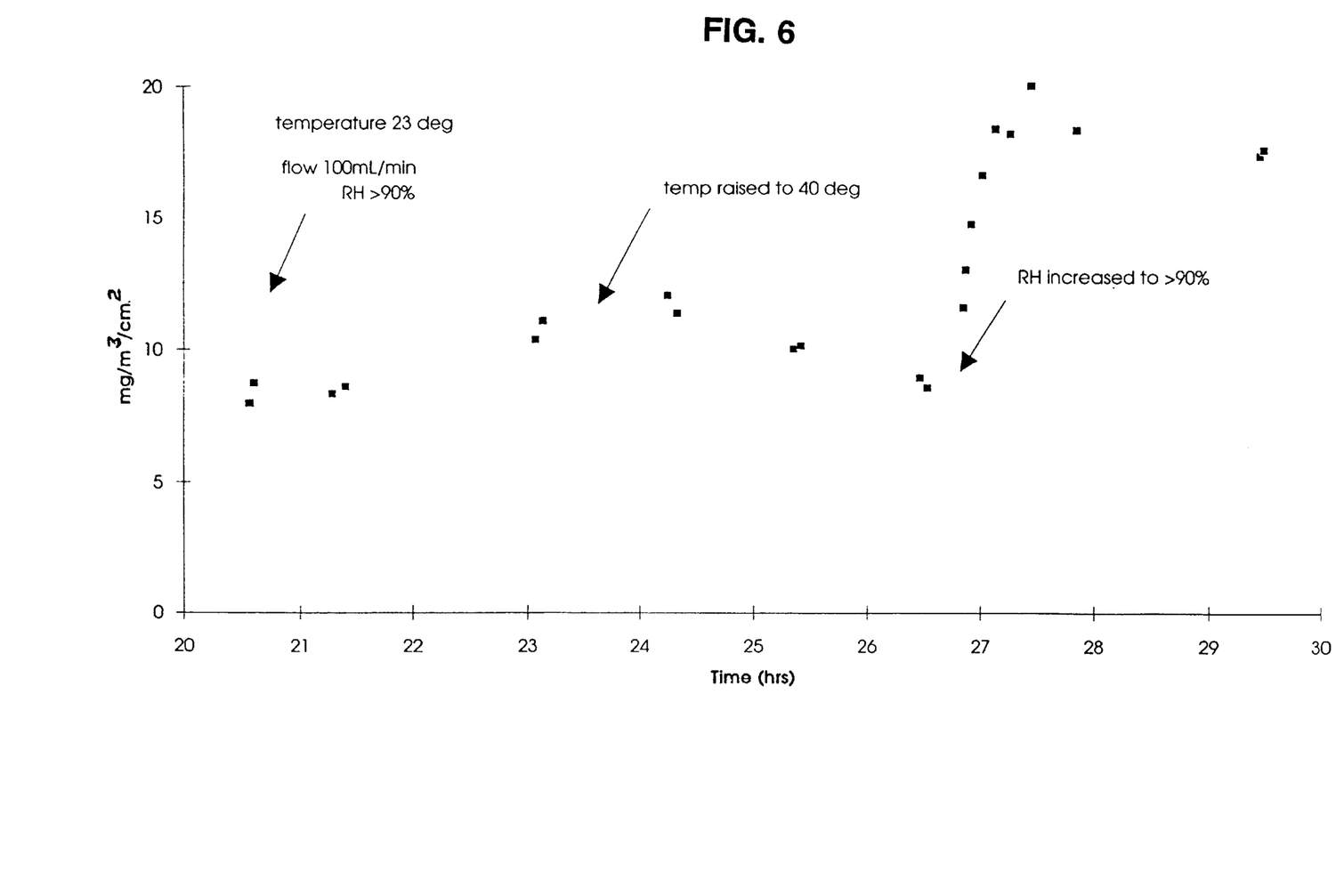
FIG. 6 illustrates the way in which phosphine production from a tray containing a phosphide formulation exposed to moist air varies when the temperature and moisture content of the air are changed.

In another experiment, trays containing identical samples of a formulation comprising 73 per cent aluminium phosphide and 27 per cent paraffin oil were exposed to an airflow of moist air and the phosphine production rate was monitored when, after steady state conditions had been established, the temperature and moisture content of the air were varied. In the first 23.5 hours of the experiment, the air of the airflow had a temperature of 23° C. and a relative humidity of greater than 90 per cent. After 23.5 hours, the air temperature was increased to 40° C. but the moisture content of the air was unaltered. After 26.5 hours, the moisture content of the air at 40° C. was increased, so that the air again had a relative humidity of greater than 90 per cent (that is, the water content of the air was increased from about 20 gm·m$^{-3}$ to about 45 gm·m$^{-3}$).

The data obtained in this experiment are presented in FIG. 6. As will be seen from this data, there was no significant increase in the rate of production of phosphine when, after 23.5 hours, the air temperature was increased but the water content was unchanged. However, increasing the moisture content of the airflow after 26.5 hours produced a dramatic increase in the phosphine production rate.

Further experiments, to investigate the potential of packaged formulations to fumigate grain silos over periods of (i) 10 to 12 days, and (ii) 25 to 30 days (in accordance with the fumigation method described in the specification of International patent application No. PCT/AU90/00268, which is WIPO Publication No. WO 91/0017), were conducted with trays of formulations exposed to saturated air (obtained by bubbling air at ambient temperature through a water bath, also at ambient temperature). Over the extended periods of these experiments, there was some variation of the ambient temperature, and hence of the moisture content of the air and the rate of production of phosphine (which was measured in terms of micrograms of phosphine produced per hour per square centimeter of exposed formulation surface). The relevant data for two experiments (one lasting 10 days, the other lasting 25 days) are presented in FIGS. 7 and 8.

Figure 7:
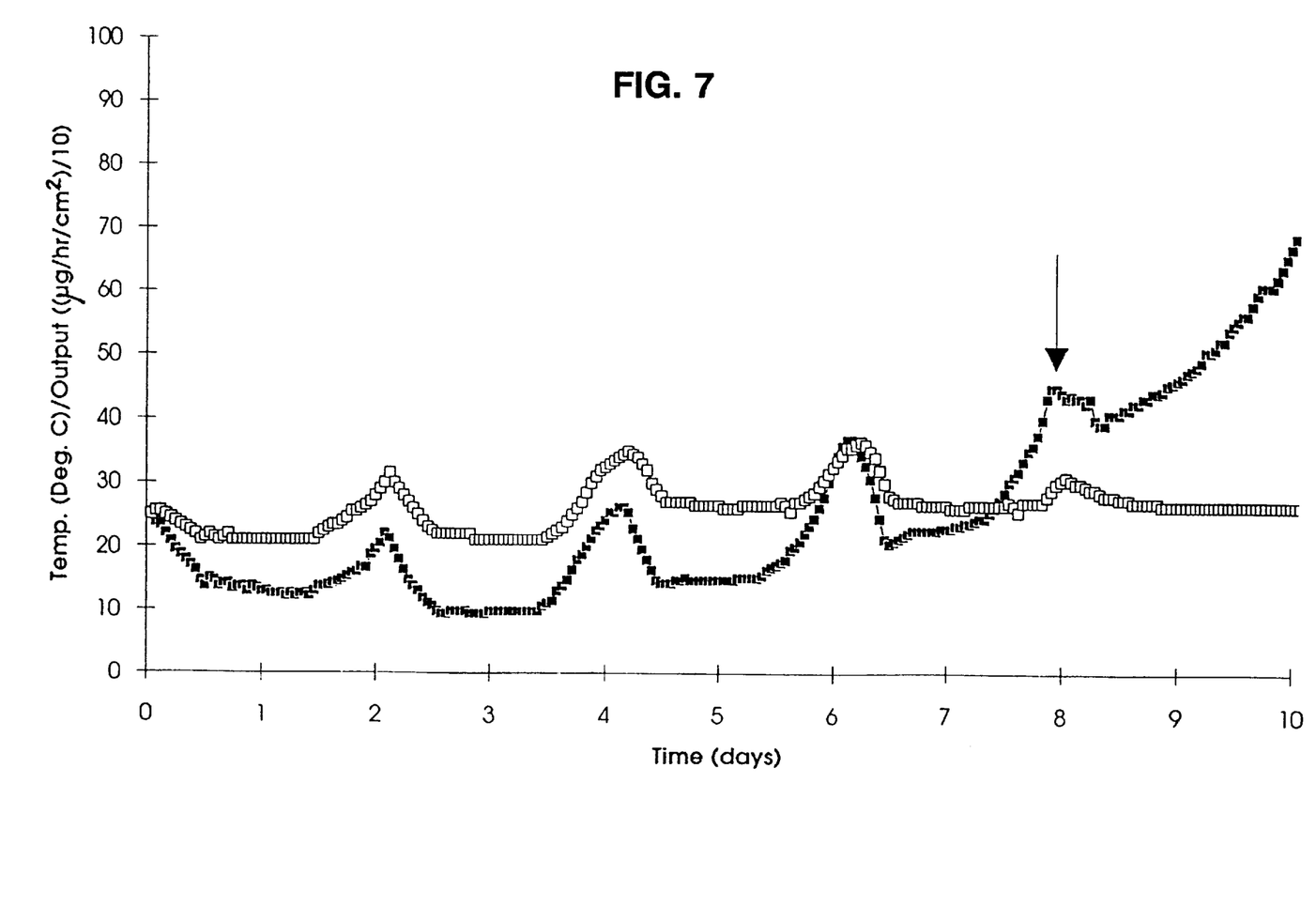
FIGS. 7 and 8 show the variation of the output of phosphine from respective trays containing samples of phosphide formulations, when the trays are exposed to moist air of varying temperature, over extended periods.

The data in FIG. 7 were obtained using a formulation which comprised 80 per cent aluminium phosphide and 20 per cent paraffin oil. The solid squares in FIG. 7 show the variation of phosphine output with time; the open squares represent the measurements of ambient temperature. The apparent perturbation of the phosphine output at approximately 8 days after the experiment started was due to a phenomenon that had also been observed with smaller samples of other formulations containing 80 per cent aluminium phosphide, exposed to moisture-containing air flows. This phenomenon is an apparent breakdown of the paste structure of the formulation, due to the powdery nature of the aluminium hydroxide formed by the reaction of the aluminium phosphide with water vapour. The aluminium hydroxide expands as it becomes more powdery, with the result that there is an increase in the surface of the formulation that is exposed to the airflow, and consequently an increase in the rate of production of phosphine.

This phenomenon (the expansion of the hydroxide) was subsequently shown to be of benefit when wax-based formulations in accordance with the present invention were used to generate phosphine. The wax matrix in which the phosphide particles are dispersed, which is the water-immiscible compound of the formulation, prevents break-up of the phosphide particles into smaller particles as the hydroxide is formed. In the manner explained earlier in this specification, the wax-based formulations maintain an essentially constant surface area of exposed phosphide particles, and thus an essentially constant rate of phosphine production over a period of time, as additional phosphide particles in the formulation become exposed.

Figure 8:
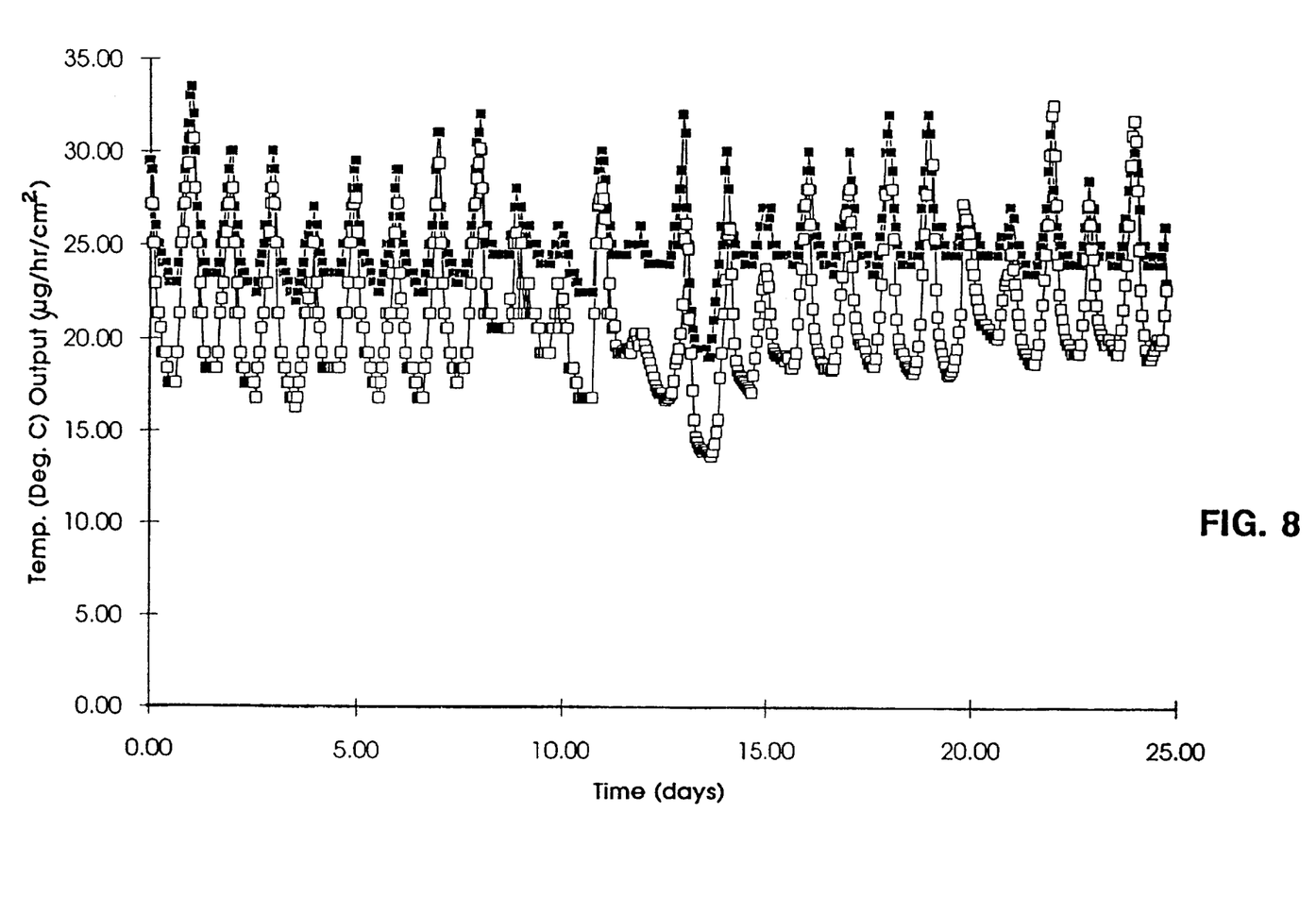

The data in FIG. 8 were obtained using a formulation comprising 73 per cent aluminium phosphide and 27 per cent paraffin oil. In FIG. 8, the solid squares represent the ambient temperature measurements and the open squares show the rate of production of phosphine. In this experiment, it would appear that the additional paraffin oil in the formulation prevented the breaking and expansion of the phosphide particles in the formulation, due to the production of aluminium hydroxide, for phosphine was produced at a consistent rate for the entire 25 days of the experiment.

Figure 9:
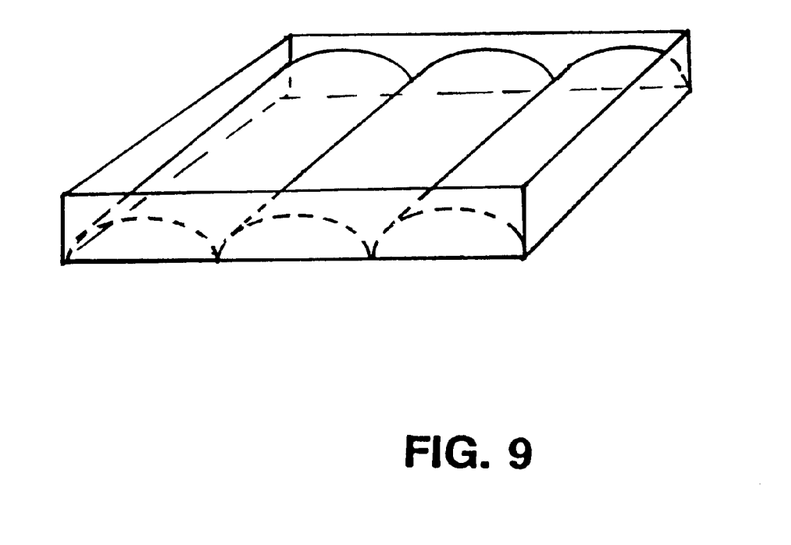
FIG. 9 illustrates one preferred form of packaged formulation, having a profile which ensures a uniform rate of phosphine generation as the phosphide in the formulation is "used up".

The apparent problem caused by the expansion of the aluminium phosphide in some formulations having petroleum jelly and/or a non-volatile oil as the water-immiscible compound, which results in the increased production of phosphine as the phosphide in the formulation is "used up", can be overcome by packaging the formulation so that it has a convex surface when exposed to moist air (for example, forming the formulation into a series of ridges, as shown in FIG. 9). This form of packaging results in the greatest area of the formulation being exposed to the airflow initially, and a decrease of the exposed area of the formulation when the aluminium phosphide in the outer region has completely reacted with the water in the airflow. As the area of formulation is reduced, expansion of the phosphide particles, due to the production of powdery aluminium hydroxide within these particles, increases the area presented to the airflow. Choosing an appropriate profile for the convex surface or surfaces of the formulation thus enables an essentially uniform production rate of phosphine to be maintained as the formulation is "used up".

Other methods of ensuring an essentially uniform production rate of phosphine with formulations which act in the manner illustrated in FIG. 7 include:

(a) presenting the formulation in layers having different compositions, with the outermost layer having the highest content of aluminium phosphide and the innermost layer having the lowest concentration of aluminium phosphide; and (b) placing the formulation in one or more small boxes, having tapered walls, so that when the phosphide in the outer (uppermost) region of the formulation has completely reacted with the water in the airflow, a smaller area of active formulation is presented to the airflow.

It will be apparent that although a variety of packaging arrangements may be used to produce the packaged formulation of the present invention, it is essential that the material of the container (including any closure member that may form part of the container) is impermeable to water and water vapour, and is chemically inert with respect to phosphides and with respect to the other materials or materials used to prepare the formulation. Preferably the container will be sufficiently robust to enable the packaged phosphide formulations to be transported to remote areas and handled in the normal manner, without the likelihood of rupturing the container, or the inadvertent opening or removal of the removable region (or one of the removable regions) of the container. One particularly suitable construction comprises a thick aluminium foil tray, with a foil lid or closure member which is removably bonded to the tray. Other suitable containers are generally flat cans with removable regions formed in a known manner in the upper surface thereof, the removal of those regions being effected by applying a force to a tag attached to the removable region. Alternatively, waxed cardboard containers, or plastic containers, with removable lids, or having apertures closed by foil or by plastic closure members lightly bonded to the container using a suitable adhesive, may be used as containers of phosphide formulations. These examples are not intended to be exhaustive, or limiting as to the form of construction of the container of a phosphide formulation.

Figure 10:
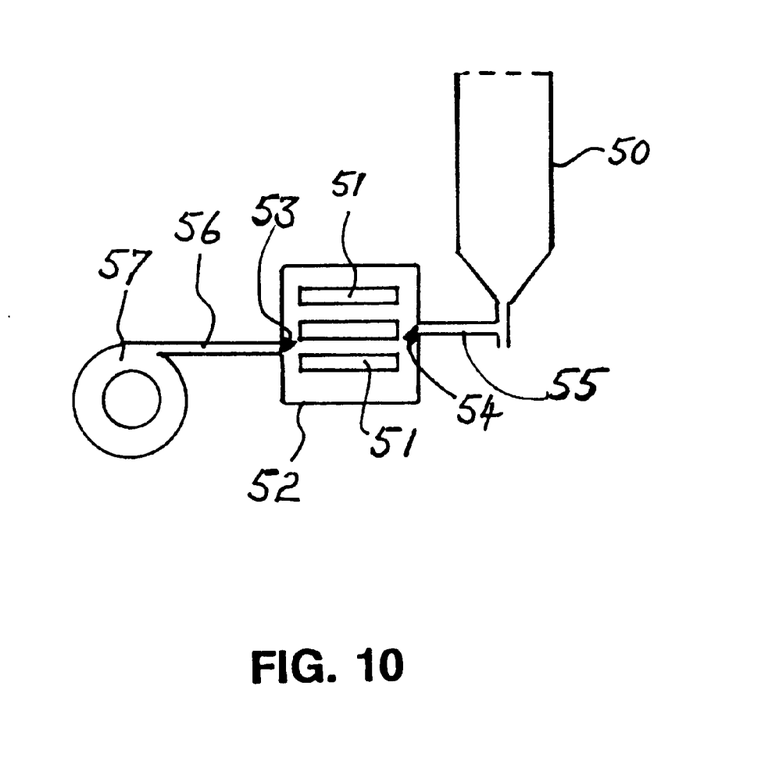
FIG. 10 is a schematic diagram, showing one way in which the packaged formulations of the present invention may be used in a fumigation system for a vertical grain silo.

FIG. 10 shows one way in which the packaged formulations of the present invention may be used in the fumigation of a vertical silo of stored grain or the like. It is emphasised that fumigation of a silo represents only one application of the present invention, which can be used in the fumigation of other enclosures and structures, such as a shed, a barn, a railway wagon, a house or a covered bag-stack (this list is not exhaustive).

In the arrangement shown in FIG. 10, a series of containers 51 of a phosphide formulation in accordance with the present invention are placed on racks in a chamber having a gas inlet port 53 and a gas outlet port 54. The outlet port is connected by a duct 55 to a gas inlet at the base of a vertical silo 50. The gas inlet port 53 is connected via a duct 56 to a blower or fan 57, which supplies air to the chamber 52.

Each of the containers 51 has its removable surface region (or at least one of its removable surface regions) removed. Thus air blown into the silo 50 by the fan 51 passes over the containers 51 and some of the moisture in the air contacts one of the exposed surfaces of the formulation. On contacting the phosphide particles of the formulation, the moisture in the airflow reacts with exposed phosphide particles to produce phosphine. The phosphine so produced is then swept into the air flowing past the containers and (via duct 55) into the grain mass in the silo 50.

As noted above, the size (and number) of the containers 51, the amount of phosphide formulation in each container, the exposed area of the formulation, and the moisture content of the air being blown into the silo are the basic parameters that determine the rate at which phosphine is generated, and the duration of such phosphine generation. Thus a person of reasonable skill in the fumigation field can readily assess the required arrangement for effective fumigation of the silo 50—and for effective fumigation of a grain silo using the arrangements illustrated in FIGS. 14 and 15 of the aforementioned specification of International patent application No. PCT/AU93/00270 (WIPO Publication No. WO 93/25075), details of which are incorporated into this specification by this reference thereto.

It will be apparent to persons who are familiar with phosphine fumigation that, although specific examples of the present invention have been described above, modifications to and variations from those exemplary embodiments may be made without departing from the present inventive concept.

We claim:

1. A phosphide formulation for use in a controlled production of phosphine, said phosphide formulation comprising a mixture of:

a) a particulate phosphide which reacts with water to form phosphine; and b) a water-immiscible compound which is inert with respect to the phosphide, said water-immiscible compound being selected from the group consisting of (i) petroleum jelly; (ii) a non-volatile oil; (iii) a mixture of a non-volatile oil and petroleum jelly; and (iv) a wax;

the particulate phosphide in the phosphide formulation comprising from 65 per cent by weight to 85 per cent by weight of the phosphide formulation.

2. A phosphide formulation as defined in claim 1, in which the particulate phosphide comprises from 70 per cent by weight to 75 per cent by weight of the phosphide formulation.

3. A phosphide formulation as defined in claim 1, wherein the phosphide formulation further comprises a surfactant, wherein the surfactant comprises up to 10 per cent by weight of the phosphide formulation.

4. A phosphide formulation as defined in claim 3, in which the surfactant comprises polyethylene glycol.

5. A phosphide formulation as defined in claim 1, in which the particulate phosphide has a particle size of less than 250 μm.

6. A phosphide formulation as defined in claim 1, in which the phosphide comprises aluminum phosphide, magnesium phosphide, or other metallic phosphide.

7. A packaged phosphide formulation comprising a moisture-impervious container and a phosphide formulation as claimed in claim 1, wherein the phosphide formulation is packaged within the moisture-impervious container, wherein the moisture-impervious container has an aperture that is closed by a closure member, and wherein the closure member is removable to expose the phosphide formulation packed in the moisture-impervious container.

8. A packaged phosphide formulation as defined in claim 7, wherein the water-immiscible compound is petroleum jelly and/or a non-volatile oil, wherein the phosphide formulation has a consistency of a stiff paste, and wherein the phosphide formulation is arranged within the moisture-impervious container so that the phosphide formulation presents at least one convex surface when the closure member is removed to expose the phosphide formulation.

9. A method of generating phosphine in a controlled manner, said method comprising:
causing a small quantity of a phosphide formulation as claimed in claim 1 to be introduced periodically into a water bath, whereby the water bath removes the water-immiscible compound from the phosphide formulation so that the phosphide particles are contacted by water of the water bath, whereupon the phosphide particles react with the water of the water bath to produce phosphine.

10. A method of generating phosphine in a controlled manner, said method comprising the steps of:
a) removing the closure member from the packaged phosphide formulation claimed in claim 7 to expose the phosphide formulation packed in the moisture-impervious container; and
b) causing a moisture-containing carrier gas to flow past the exposed phosphide formulation, thereby enabling water in the carrier gas to react with the phosphide in the phosphide formulation to form phosphine, which is incorporated into the carrier gas.

11. A method of generating phosphine within a fumigation enclosure, said method comprising placing a packaged phosphide formulation as claimed in claim 7 in the fumigation enclosure with the closure member removed to thereby expose the phosphide formulation to air or other gas within the fumigation enclosure, thereby permitting moisture in the air or the other gas within the fumigation enclosure to react with the phosphide in the phosphide formulation to form phosphine, which permeates through the fumigation enclosure.

12. A phosphide formulation for use in controlled production of phosphine, the phosphide formulation comprising a mixture of:
a) a phosphide, wherein the phosphide comprises magnesium phosphide, aluminum phosphide, or other metallic phosphide; and
b) a compound selected from the group consisting of petroleum jelly, oil, a mixture of oil and petroleum jelly, and wax;
wherein the phosphide comprises from 65% by weight to 85% by weight of the phosphide formulation.

13. A phosphide formulation as claimed in claim 12, in which the phosphide comprises from 70 percent by weight to 75 percent by weight of the phosphide formulation.

14. A phosphide formulation as claimed in claim 12, the phosphide formulation further comprising a surfactant, said surfactant comprising up to 10 percent by weight of the phosphide formulation.

15. A phosphide formulation as claimed in claim 12, in which the surfactant comprises polyethylene glycol.

16. A phosphide formulation as claimed in claim 12, in which the phosphide has a particle size of less than 250 $\mu$m.

17. A packaged phosphide formulation comprising a moisture-impervious container and a phoshide formulation as claimed in claim 12, wherein the phosphide formulation is packaged within the moisture-impervious container, wherein the moisture-impervious container has an aperture that is closed by a closure member.

18. A packaged phosphide formulation as claimed in claim 17, wherein said closure member is removable to expose the phosphide formulation packed in the moisture-impervious container.

19. A phosphide formulation as claimed in claim 12, wherein the compound is the oil or the wax.

20. A phosphide formulation as claimed in claim 1, wherein the water-immiscible compound is the non-volatile oil or the wax.

21. A method as claimed in claim 9, wherein the water-immiscible compound is the wax.

22. A packaged phosphide formulation as claimed in claim 18, wherein the compound is petroleum jelly and/or a non-volatile oil, wherein the phosphide formulation has a consistency of a paste, and wherein the phosphide formulation is arranged within the moisture-impervious container so that the phosphide formulation presents at least one convex surface when the closure member is removed to expose the phosphide formulation.

23. A packaged phosphide formulation as claimed in claim 18, wherein the compound is petroleum jelly and/or a non-volatile oil, wherein the phosphide formulation has a consistency of a paste, wherein the phosphide formulation is arranged within the moisture-impervious container so that the phosphide formulation presents at east one convex surface when the closure member is removed to expose the phosphide formulation.

24. A method of generating phosphine in a controlled manner, said method comprising:
causing a quantity of a phosphide formulation as claimed in claim 12 to be introduced into a water bath, whereby the water bath removes the compound from the phosphide formulation so that the phosphide is contacted by the water of the water bath, whereupon the phosphide reacts with the water of the water bath to produce phosphine.

25. A method as claimed in claim 23, in which the water in the water bath contains a detergent.

26. A method of generating phosphine in a controlled manner, said method comprising the steps of:
(a) removing the closure member from the packaged phosphide formulation claimed in claim 18 to expose the phosphide formulation packed in the moisture-impervious container; and
(b) causing a moisture-containing carrier gas to flow past the exposed phosphide formulation, thereby enabling water in the carrier gas to react with the phosphide in the phosphide formulation to form phosphine, which is incorporated into the carrier gas.

27. A method of generating phoshine within a fumigation enclosure, said method comprising placing a packaged phosphide formulation as claimed in claim 18 in the fumigation enclosure with the closure member removed to thereby expose the phosphide formulation to air or other gas within the fumigation enclosure, thereby permitting moisture in the air or the other gas within the fumigation enclosure to react with the phosphide in the phosphide formulation to for phosphine, which permeates through the fumigation enclosure.

28. A phosphide formulation as claimed in claim 12, wherein the compound is the oil or the wax.

29. A method as claimed in claim 23, wherein the water-immiscible compound is the wax.

30. A method of generating phosphine in a controlled manner, said method comprising the steps of:
exposing the phosphide formulation claimed in claim 12 to a moisture-containing carrier gas, thereby enabling water in the carrier gas to react with the phosphide in the phosphide formulation to form phosphine, wherein the phosphine is incorporated into the carrier gas, wherein the phosphide formulation comprises the phosphide and the compound, and wherein the compound is the wax.

31. A phosphide formulation as claimed in claim 1, wherein the phosphide formulation is extrudable.

* * * * *